(12) United States Patent
Te et al.

(10) Patent No.: US 10,780,424 B2
(45) Date of Patent: Sep. 22, 2020

(54) CRUSH STRENGTH AND POROSITY OF AN ALUMINA CARRIER FOR ENHANCED VAM CATALYSTS

(71) Applicant: LyondellBasell Acetyls, LLC, Houston, TX (US)

(72) Inventors: Mure Te, Pearland, TX (US); Daniel F. White, Houston, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 548 days.

(21) Appl. No.: 15/814,042

(22) Filed: Nov. 15, 2017

(65) Prior Publication Data

US 2018/0133696 A1 May 17, 2018

Related U.S. Application Data

(60) Provisional application No. 62/423,642, filed on Nov. 17, 2016.

(51) Int. Cl.
*B01J 23/58* (2006.01)
*B01J 23/66* (2006.01)
(Continued)

(52) U.S. Cl.
CPC ............... *B01J 23/66* (2013.01); *B01J 21/04* (2013.01); *B01J 23/52* (2013.01); *B01J 23/58* (2013.01); *B01J 31/04* (2013.01); *B01J 35/002* (2013.01); *B01J 35/0006* (2013.01); *B01J 35/0026* (2013.01); *B01J 35/026* (2013.01);
(Continued)

(58) Field of Classification Search
CPC ... B01J 21/04; B01J 23/52; B01J 23/58; B01J 31/04; B01J 35/0006; B01J 35/002; B01J 35/0026; B01J 35/026; B01J 35/1009; B01J 35/1014; B01J 35/1038; B01J 35/1066; B01J 35/1071; B01J 37/0201; B01J 37/0203; B01J 37/0236; B01J 37/031; B01J 37/033; B01J 37/035; B01J 37/06;
(Continued)

(56) References Cited

U.S. PATENT DOCUMENTS 3,743,607 A 7/1973 Sennewald et al.
4,119,567 A * 10/1978 Bartsch ................. C07C 67/055
502/170
(Continued)

FOREIGN PATENT DOCUMENTS

CA 2205416 C 1/2001
WO 03061829 A1 7/2003

OTHER PUBLICATIONS

The International Search Report and Written Opinion for PCT/US2017/061812 dated Mar. 16, 2018.

*Primary Examiner* — Haytham Soliman

(57) ABSTRACT

Disclosed is a supported catalyst for the preparation of vinyl acetate monomer, a process for preparing the supported catalyst in tablet or pellet form, and a catalytic process for the manufacturing vinyl acetate using the supported catalyst. Specifically, it is shown that catalyst performance shows a strong dependence on the crush strength of the tableted or pelletized alumina support used in the process to make the catalyst, and that the crush strength of the catalyst is closely related to the porosity of the support. Catalyst activity and selectivity can be enhanced by tailoring the crush strength of the support.

20 Claims, 4 Drawing Sheets

(51) Int. Cl.
*B01J 37/03* (2006.01)
*B01J 37/02* (2006.01)
*B01J 35/10* (2006.01)
*B01J 23/52* (2006.01)
*B01J 31/04* (2006.01)
*B01J 21/04* (2006.01)
*B01J 35/00* (2006.01)
*B01J 35/02* (2006.01)
*B01J 37/06* (2006.01)
*B01J 37/08* (2006.01)
*B01J 37/18* (2006.01)
*C07C 67/055* (2006.01)
*C07C 69/15* (2006.01)

(52) U.S. Cl.
CPC ....... *B01J 35/1009* (2013.01); *B01J 35/1014* (2013.01); *B01J 35/1038* (2013.01); *B01J 35/1066* (2013.01); *B01J 35/1071* (2013.01); *B01J 37/0201* (2013.01); *B01J 37/0203* (2013.01); *B01J 37/0236* (2013.01); *B01J 37/031* (2013.01); *B01J 37/033* (2013.01); *B01J 37/035* (2013.01); *B01J 37/06* (2013.01); *B01J 37/088* (2013.01); *B01J 37/18* (2013.01); *C07C 67/055* (2013.01); *C07C 69/15* (2013.01); *B01J 2523/00* (2013.01)

(58) Field of Classification Search
CPC ....... B01J 37/088; B01J 37/18; C07C 67/055; C07C 69/15
USPC .......................................................... 502/330
See application file for complete search history.

(56) References Cited

U.S. PATENT DOCUMENTS

| | | | |
|---|---|---|---|
| 4,908,343 A * | 3/1990 | Bhasin | B01J 23/66 502/208 |
| 5,808,136 A | 9/1998 | Tacke et al. | |
| 6,022,823 A | 2/2000 | Augustine et al. | |
| 7,855,304 B1 * | 12/2010 | Kaminsky | B01J 21/063 560/261 |
| 8,399,700 B2 | 3/2013 | Salisbury et al. | |
| 8,501,984 B2 | 8/2013 | Shay | |
| 2005/0032638 A1 | 2/2005 | Baker et al. | |
| 2011/0087047 A1 | 4/2011 | Hallinan et al. | |
| 2011/0137075 A1 | 6/2011 | Brtko et al. | |
| 2011/0306748 A1 * | 12/2011 | Shay | B01J 35/002 528/271 |

* cited by examiner

CRUSH STRENGTH AND POROSITY OF AN ALUMINA CARRIER FOR ENHANCED VAM CATALYSTS

CROSS REFERENCE TO RELATED APPLICATIONS

This application claims the benefit of priority to U.S. Provisional Application No. 62/423,642 filed on Nov. 17, 2016, which is incorporated herein by reference in its entirety.

TECHNICAL FIELD

This disclosure describes catalysts and processes related to the catalytic synthesis of vinyl acetate monomer.

BACKGROUND OF THE DISCLOSURE

Vinyl acetate monomer (VAM) is a large-scale commodity chemical that is used primarily to manufacture polyvinyl acetate, an important component of paints, adhesives, and coatings. Vinyl acetate can be produced by the acetoxylation of ethylene, which involves the reaction of ethylene, oxygen and acetic acid in the presence of an activated palladium-gold catalyst. This process is generally performed in a gas phase, fixed bed tubular reactor, from which the resulting vinyl acetate is recovered by condensation and purification.

Through the years, there have been many efforts to increase the catalytic activity to reduce the amount of catalyst needed, driven by factors such as the high costs of the precious metals palladium and gold used in the catalyst. For example, U.S. Pat. No. 6,022,823 discloses generally calcining a support impregnated with palladium and gold salts prior to reducing the metals, which enhances catalyst activity.

Issues related to improving the overall efficiency and economics of the process remain, despite various advances in improving catalytic activity. Therefore, there is a need to identify new methods, catalyst compositions and properties, and process parameters that can further enhance the catalytic production of vinyl acetate monomer.

SUMMARY OF THE DISCLOSURE

This disclosure provides generally a supported catalyst in tablet or pellet form for the preparation of vinyl acetate monomer, a process for preparing the supported catalyst, and a catalytic process for the manufacturing vinyl acetate using the supported catalyst. Specifically, it has been discovered unexpectedly that catalyst performance showed a strong dependence on the crush strength of the tableted or pelletized catalyst, and that crush strengths that are too high are detrimental to catalyst performance and selectivity. Further investigations led to the discovery that the crush strength of the catalyst is closely related to the porosity of the tableted catalyst carrier or support, and that porosity can be limited by the tableting process and sintering conditions to achieve the required mechanical strength or crush strength for the carrier.

In one aspect, this disclosure provides a method to achieve high catalyst performance in VAM production, by manufacturing the carrier, such as a tableted or pelletized alumina carrier or support, with a defined porosity, specifically, a porosity that is high enough to allow an effective precious metal dispersion in the catalyst preparation, but also low enough to allow sintering of the carrier to provide sufficient mechanical strength to the catalyst. Therefore, there is provided a process for preparing a supported catalyst, the process comprising:

a) providing an alumina support in tablet form having an average crush strength of greater than about 8 lbf/mm and less than about 12 lbf/mm (pound-force per millimeter, measured by ASTM 6175-03), a pore volume (measured by Mercury Intrusion Porosimetry, HgPV) from 0.25 mL/g to 0.35 mL/g, and a crystalline $\alpha$-alumina content of greater than 93%;

b) contacting the alumina support with a composition to provide an impregnated alumina support, the composition comprising [1] a palladium salt and a gold salt, and [2] a fixing agent selected from an alkali metal, an alkaline earth metal, or an ammonium compound of hydroxide, carbonate, bicarbonate, or metasilicate, or any combination thereof;

c) calcining the impregnated alumina support in a non-reducing atmosphere for a time and a temperature sufficient to at least partially decompose the palladium salt and the gold salt; and d) reducing the calcined impregnated alumina support comprising partially decomposed palladium and gold salts with a reducing agent for a time and a temperature sufficient to provide a supported catalyst comprising palladium metal and gold metal.

After the alumina support is contacted with the palladium salt and the gold salt composition, the impregnated support is typically dried, washed with water to remove soluble ions such as chloride ion, and dried again before the impregnated support is calcined in a non-reducing atmosphere.

In a further aspect, a process for the production of vinyl acetate comprising reacting ethylene, acetic acid, and oxygen in the presence of a supported catalyst prepared according to the disclosure is provided, to produce a reaction mixture comprising vinyl acetate. This summary and the following detailed description set out specific embodiments and aspects of the invention. Additional features or variations thereof can be provided in addition to those set forth in this disclosure, such as for example, various feature combinations and sub-combinations of those features as described in the detailed description.

BRIEF DESCRIPTION OF THE DRAWINGS

In order to fully describe features of the present disclosure, reference is made to the following figures, with the understanding that these drawings depict exemplary embodiments and aspects of this disclosure and are to be considered non-limiting.

DETAILED DESCRIPTION

Figure 1:
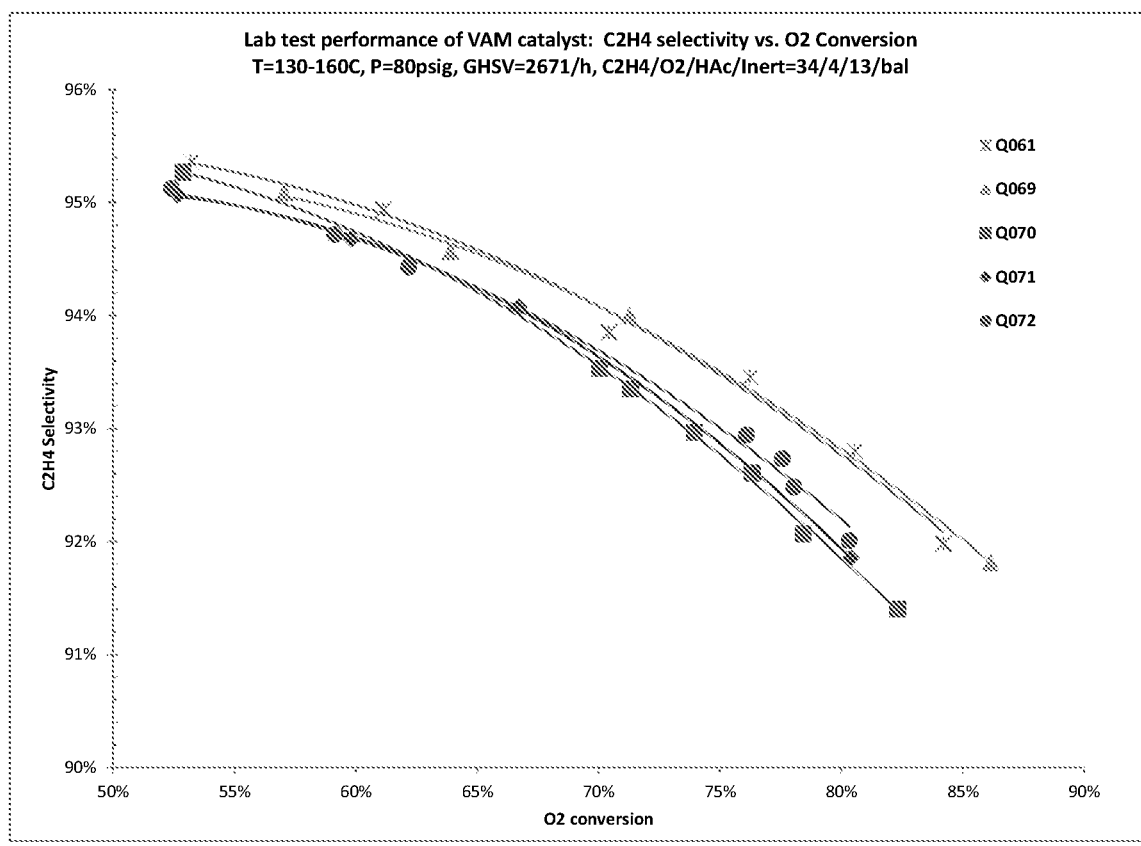
FIG. 1 presents a plot of ethylene ($C_2H_4$) selectivity (%) versus $O_2$ conversion (%) for the vinyl acetate monomer (VAM) catalysts presented in Example 2 and Table 1.

Several aspects and embodiments of the process for the production of vinyl acetate monomer (VAM) by reacting ethylene, acetic acid, and oxygen in the presence of a supported catalyst are set out in this disclosure, particularly the process for preparing a supported VAM catalyst. This disclosure particularly addresses the supported palladium-gold VAM catalysts and improved methods for preparing the palladium-gold catalysts. U.S. Pat. No. 4,119,567 provides general procedures for catalyst preparation, and U.S. Pat. No. 6,022,823 describes some improvements to the general methods, for example, calcining the support impregnated with palladium and gold salts prior to reducing the metals. The palladium-gold catalyst generally can be supported on an inorganic oxide, for example, an inorganic oxide comprising or selected from alumina, silica, titania, and the like, or mixtures thereof.

It has been unexpectedly discovered that, contrary to conventional thought, crush strength of a tableted carrier can be detrimental to catalyst performance if it exceeds a certain threshold. Therefore, catalyst performance and selectivity were found to fall off if carrier crush strengths were too high, and also the catalysts would not have sufficient mechanical strength if the crush strengths were too low. Investigations showed that the porosity of the tableted alumina carrier also depends on the crush strength, therefore, the catalyst performance is directly related to the porosity of the carrier and the catalyst can be tailored by altering the porosity of the catalyst carrier which, in turn, can be customized according to the tableting conditions and calcination conditions.

Because crush strength of the catalyst is related to the porosity of the catalyst carrier, to achieve high catalyst performance in VAM production, an alumina carrier is employed having a porosity that is high enough to allow an effective precious metal dispersion in the catalyst preparation, but not so high that it adversely affects the mechanical strength to the catalyst. In accordance with this discovery, there is provided a process for preparing a supported catalyst, the process comprising:

a) providing an alumina support in tablet form having an average crush strength of greater than about 8 lbf/mm and less than about 12 lbf/mm, a pore volume (mercury intrusion porosimetry) from 0.25 mL/g to 0.35 mL/g, and a crystalline α-alumina content of greater than 93%;

b) contacting the alumina support with a composition to provide an impregnated alumina support, the composition comprising [1] a palladium salt and a gold salt, and [2] a fixing agent selected from an alkali metal, an alkaline earth metal, or an ammonium compound of hydroxide, carbonate, bicarbonate, or metasilicate, or any combination thereof;

c) calcining the impregnated alumina support in a non-reducing atmosphere for a time and a temperature sufficient to at least partially decompose the palladium salt and the gold salt; and d) reducing the calcined impregnated alumina support comprising partially decomposed palladium and gold salts with a reducing agent for a time and a temperature sufficient to provide a supported catalyst comprising palladium metal and gold metal.

After the alumina support is contacted with the composition comprising the palladium salt, the gold salt and the additional alkali metal, alkaline earth metal, or ammonium compound, the impregnated support is typically dried, washed with water to remove soluble ions such as chloride ion, and dried again before the impregnated support is calcined in a non-reducing atmosphere. Therefore, in this aspect, the process for preparing a supported catalyst can further comprise, following the contacting step b) and before the calcining step c), the further steps of drying the impregnated alumina support, washing it with water, and drying it again after washing.

Figure 3:
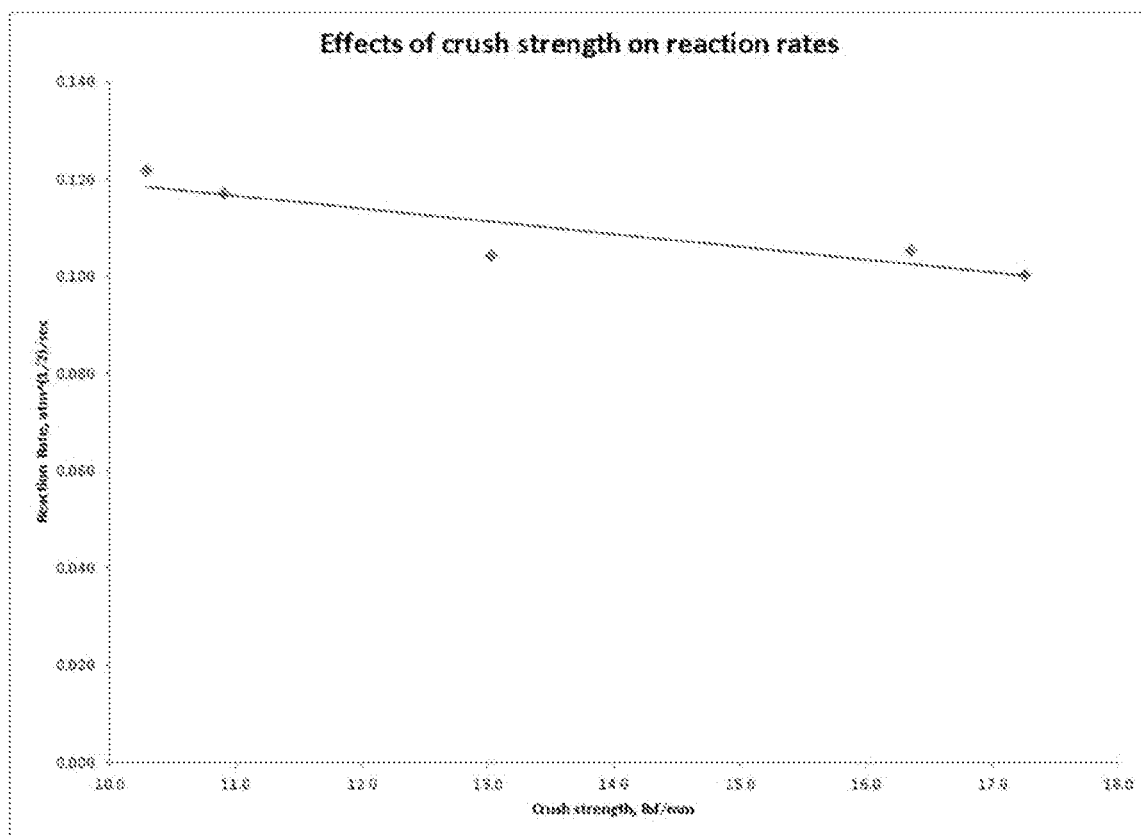
FIG. 3 illustrates the effect of crush strength (lbf/mm) on reaction rates ($atm^{1/2}$/sec at 150° C.) for the catalysts presented in Example 2 and Table 1.

The average crush strength of the tableted or pelletized alumina support is greater than about 8 lbf/mm and less than about 12 lbf/mm, for the improved performance. Referring to FIG. 1, it is seen in this plot of ethylene ($C_2H_4$) selectivity (%) versus $O_2$ conversion (%) for producing vinyl acetate monomer (VAM) on the new catalysts, that the catalysts Q069 and Q061 exhibited the best performance in ethylene selectivity as a function of oxygen conversion. The Table 1 data reveals that the best performance in ethylene selectivity as a function of oxygen conversion occurred when the alumina supported catalyst crush strength is about 10.6 lbf/mm. Catalysts Q069 and Q061 have alumina pellet crush strengths of 10.9 lbf/mm and 10.3 lbf/mm, respectively, and these catalysts provide selectivity (FIG. 1) and reaction rates (Table 1, FIG. 3) that are substantially improved over the catalysts prepared using alumina pellets having crush strengths of 13 lbf/mm and greater.

Figure 2:
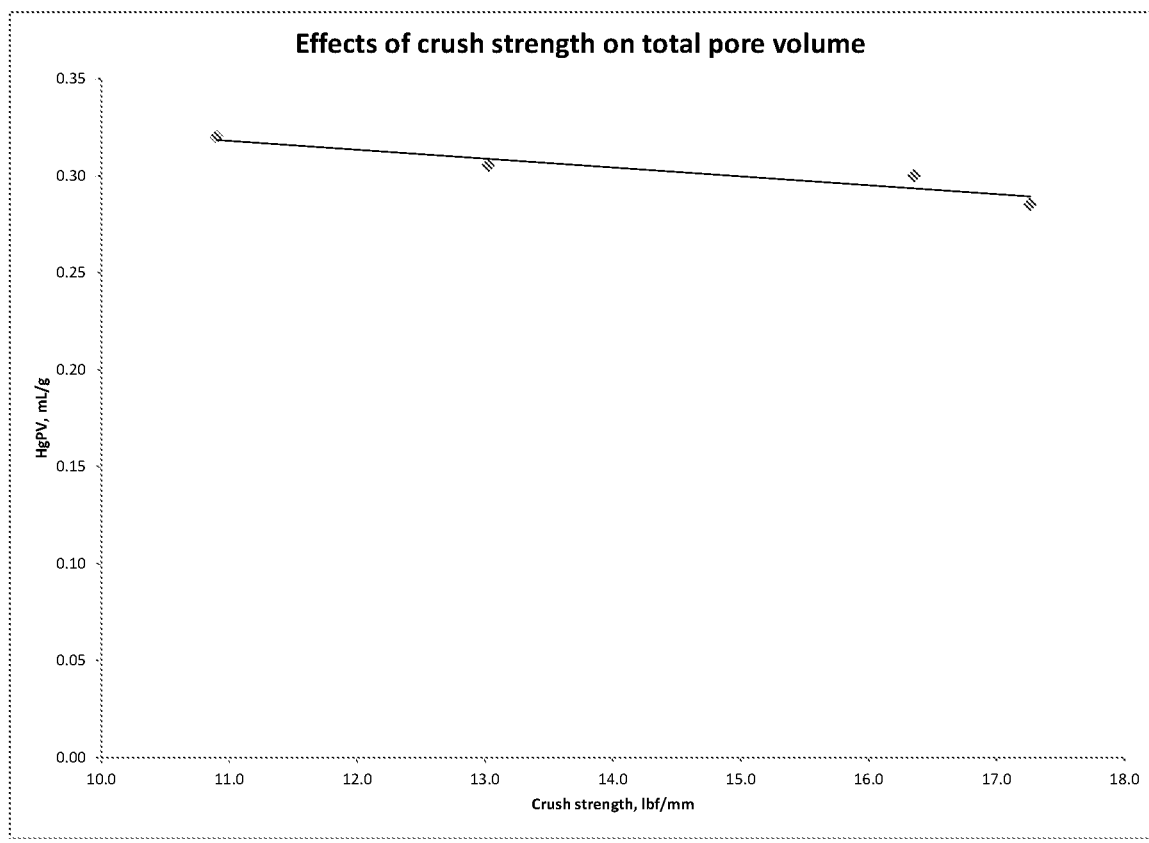
FIG. 2 illustrates the effect of crush strength (lbf/mm) on total pore volume (HgPV, mL/g) for the catalysts presented in Example 2 and Table 1.

Further investigation revealed that the catalyst crush strength is directly related to the pore volume measured by Mercury Intrusion method (HgPV), as illustrated in FIG. 2. While not intending to be theory-bound, it is thought that whereas a high pore volume may be beneficial, a high pore volume achieved with less sintering of the alumina phase may weaken its mechanical strength and reduce the alumina carrier's surface inertness, which may be detrimental to the catalyst performance. This is likely because the resulting low mechanical strength may lead to process issues, while the more active alumina surface may lead to increased production of unwanted side products at the expense of VAM selectivity.

Accordingly, suitable tableted or pelletized alumina supports and catalysts of this disclosure can be characterized by average crush strengths of from about 8 lbf/mm to about 12 lbf/mm, or greater than about 8 lbf/mm and less than about 12 lbf/mm. That is, alumina supports and catalyst crush strengths can be about 8 lbf/mm, about 8.5 lbf/mm, about 9 lbf/mm, about 9.5 lbf/mm, about 10 lbf/mm, about 10.5 lbf/mm, about 11 lbf/mm, about 11.5 lbf/mm, or about 12 lbf/mm, including any ranges or combinations of subranges between any of these crush strength values. For example, the average crush strengths can also be from about 8.5 lbf/mmlbs to about 11.5 lbf/mm; alternatively, from about 9 lbf/mm to about 11 lbf/mm; or from about 10 lbf/mm to about 11 lbf/mm.

Suitable tableted or pelletized alumina supports of this disclosure also can be characterized by specific beneficial pore volumes (mercury intrusion porosimetry), abbreviated HgPV, of from about 0.25 mL/g to about 0.35 mL/g. That is, pore volumes (HgPV) of the alumina supports of this disclosure can be about 0.25 mL/g, about 0.26 mL/g, about 0.27 mL/g, about 0.28 mL/g, about 0.29 mL/g, about 0.30 mL/g, about 0.31 mL/g, about 0.32 mL/g, about 0.33 mL/g, about 0.34 mL/g, or about 0.35 mL/g, including any ranges or combinations of subranges between any of these HgPV values. For example, suitable pore volumes (HgPV) of the tableted alumina supports also can be from about 0.26 mL/g to about 0.34 mL/g; from about 0.27 mL/g to about 0.33 mL/g; from about 0.28 mL/g to about 0.35 mL/g; from about 0.29 mL/g to about 0.34 mL/g; from about 0.30 mL/g to about 0.35 mL/g; or from about 0.32 mL/g to about 0.35 mL/g. The pore volumes of the alumina supports are measured according to the ASTM D4284-12, Standard Test Method for Determining Pore Volume Distribution of Catalysts and Catalyst Carriers by Mercury Intrusion Porosimetry. The alumina supports also can have a range of pore size (diameter) distributions. For example, the pore size (diameter) distribution curve as measured by mercury intrusion porosimetry can have relative maximums from about 0.05 to about 1 micrometer (µm).

Suitable tableted alumina supports can have a wide range of surface area values. For example, the alumina support can have a surface area of from 1 $m^2/g$ to 25 $m^2/g$, including any value between these $m^2/g$ surface area values. These values are presented as exemplary, as the alumina support is not required to have surface area values within this range.

The tableted alumina support has also been found to provide good activity and selectivity when the crystalline α-alumina content is generally greater than about 93%. For example, the alumina support can have a crystalline α-alumina content of greater than or about 93%, greater than or about 94%, greater than or about 95%, greater than or about 96%, greater than or about 97%, greater than or about 98%, or greater than or about 99%.

The process for preparing a supported catalyst according to this disclosure includes a step of contacting the tableted alumina support as described with a palladium salt and a gold salt to provide an impregnated alumina support. In this aspect, exemplary palladium salts can comprise or can be selected from palladium chloride, sodium chloropalladite, palladium nitrate, or palladium sulfate or combinations thereof, although other palladium salts and compounds can be employed. Exemplary gold salts can comprise or can be selected from auric chloride, tetrachloroauric acid, or sodium tetrachloroaurate, or combinations thereof, although other gold salts also may be used.

Following the impregnation step, the impregnated alumina support is dried, for example, at temperatures above room temperature and at atmospheric pressure or under vacuum. For example, drying can be carried out at from about 40° C. to about 150° C. under atmospheric pressure conditions, or alternatively, from about 60° C. to about 130° C. or from about 80° C. to about 110° C., under atmospheric pressure conditions. Following drying, the impregnated support is washed with water, typically hot (greater than room temperature and up to its boiling point) water, to remove soluble ions such as chloride ion. Washing can be conducted, for example, until the wash water provides a negative chloride test with silver nitrate. Following washing, another drying step can be carried out prior to calcining.

Once the washed and dried impregnated alumina support is obtained, the process for preparing the supported catalyst also includes a step of calcining the impregnated alumina support in a non-reducing atmosphere for a time and a temperature sufficient to at least partially decompose the palladium salt and the gold salt. Non-reducing atmospheres can comprise or can be selected from, for example, an inert gas or an oxidizing gas. Examples of suitable gases include, but are not limited to, helium, nitrogen, argon, neon, nitrogen oxides, oxygen, air and carbon dioxide and the like.

The calcining step is also appreciated by the person of ordinary skill. For example, the calcining step temperature can be from about 100° C. to about 600° C. Commonly used temperatures include, but are not limited to, about 100° C., about 150° C., about 200° C., about 250° C., about 300° C., about 350° C., about 400° C., about 450° C., about 500° C., about 550° C., or about 600° C., including ranges therebetween. Generally, when the calcining step is conducted at a temperature from about 100° C. to about 600° C., at least a portion of both the palladium salt and the gold salt is decomposed. For example, from about 10 mol % to about 70 mol % of the palladium salt and the gold salt, independently, can be decomposed under these conditions, or alternatively, from about 20 mol % to about 60 mol % of the palladium salt and the gold salt, independently, can be decomposed. That is, the calcining step generally results in the palladium and gold salts being at least partially decomposed.

Generally, the calcining times can be from about 1 h (hour) to about 7 h, from about 1.5 h to about 5 h, or from about 2 h to about 4 h. For example, in one aspect the calcining times can be about 1 h, about 1.5 h, about 2 h, about 2.5 h, about 3 h, about 3.5 h, about 4 h, about 4.5 h, about 5 h, about 5.5 h, about 6 h, about 6.5 h, or about 7 h, including any ranges between these time values.

In a further aspect, the calcining step can be conducted at a temperature and for a time such that greater than 70 mol % of the palladium salt and the gold salt, independently, can be decomposed. For example, the disclosed process includes calcining the impregnated support at a temperature from about 350° C. to about 600° C. and/or wherein at least 70 mol % of the palladium salt and at least 70 mol % of the gold salt are decomposed.

As described, the impregnated alumina support is calcined in a non-reducing atmosphere for a time and a temperature sufficient to at least partially decompose the palladium and gold salts. Subsequent to the calcining step, the calcined impregnated alumina support is subjected to a reduction (reducing) step, in which the partially decomposed palladium and gold salts are contacted or reacted with a reducing agent for a time and a temperature sufficient to provide a supported catalyst comprising palladium metal and gold metal. For example, the reducing step temperature can be from ambient to about 550° C., wherein about 5 h reducing time can be beneficially used with reducing step temperature of about 550° C. The reducing agent can comprise or can be selected from, for example, hydrogen, carbon monoxide, hydrocarbons, aldehydes, alcohols, ammonia, hydrazine, primary amines, carboxylic acids, carboxylic acid salts or carboxylic acid esters and the like.

According to an aspect, the reducing step temperature can be from ambient to about 550° C., for example, can be about 25° C., about 50° C., about 75° C., about 100° C., about 150° C., about 200° C., about 250° C., about 300° C., about 350° C., about 400° C., about 450° C., about 500° C., or about 550° C., including any ranges between these temperature values. Depending upon the reducing step temperature, the reducing step time can be from about 0.5 h to about 10 h. For example, can be about 0.5 h, 1 h, 1.5 h, 2 h, 2.5 h, 3 h, 3.5 h, 4 h, 4.5 h, 6 h, 6.5 h, 7 h, 7.5 h, 8 h, 8.5 h, 9 h, 9.5 h, or about 10 h, including any ranges between these values. Typical conditions include the catalyst being reduced at about 450-500° C. for 4.5-6 h under a flow of 5 mol % hydrogen in an argon flow (10 mL/min/g).

Following the reduction step, the resulting supported catalysts generally can have palladium contents from about 0.1 wt % to about 10 wt %; or alternatively, from about 0.1 wt % to about 5 wt %; alternatively, from about 0.1 wt % to about 3 wt %; or alternatively, from about 0.2 wt % to about 2 wt %. The resulting supported catalysts generally also can have gold contents from about 0.1 wt % to about 5 wt %; alternatively, from about 0.1 wt % to about 4 wt %; alternatively, from about 0.1 wt % to about 3 wt %; or alternatively, from about 0.2 wt % to about 1.5 wt %. For example, and not as a limitation, the supported catalysts can have from about 0.5 wt % to about 1.5 wt % of palladium and from 0.25 wt % to 0.75 wt % of gold. The weight ratio of palladium to gold can be within the range of from about 5:1 to about 1:3, from about 4:1 to about 1:2, or more generally from about 2.5:1 to about 1:1.5.

For example, the palladium content (metal basis) can be about 0.1 wt %, about 0.2 wt %, about 0.5 wt %, about 0.75 wt %, about 1 wt %, about 1.2 wt %, about 1.4 wt %, about 1.6 wt %, about 1.8 wt %, about 2 wt %, about 2.5 wt %, about 3 wt %, about 3.5 wt %, about 4 wt %, about 4.5 wt %, about 5 wt %, about 6 wt %, about 7 wt %, about 8 wt %, about 9 wt %, or about 10 wt %, including ranges between these values. Similarly, the gold content (metal basis) can be about 0.1 wt %, about 0.2 wt %, about 0.3 wt %, about 0.4 wt %, about 0.5 wt %, about 0.75 wt %, about 1 wt %, about 1.2 wt %, about 1.4 wt %, about 1.6 wt %, about 1.8 wt %, about 2 wt %, about 2.2 wt %, about 2.4 wt %, about 2.6 wt %, about 2.8 wt %, or about 3 wt %, including ranges between these values.

In some aspects, the alumina support is contacted or treated with a fixing agent when the alumina support is also contacted with the palladium compound and the gold compound. The term fixing agent is used to generally reflect the observation that such agents appear to help bind the palladium compound and the gold compound to the tableted support to produce a more robust catalyst. Suitable fixing agents can comprise or can be selected from an alkali metal, an alkaline earth metal, or an ammonium compound of hydroxide, carbonate, bicarbonate, or metasilicate, or any combination thereof. Any suitable impregnation method can be used to produce the impregnated support, and typically the support is impregnated with aqueous solutions although other impregnating solvents may be used. Following contacting the alumina support with the palladium compound, the gold compound, and the fixing agent, the impregnated support can be dried and subsequently washed with water or other solvents to remove any halide, typically chloride. For example, in an aspect, sodium hydroxide, sodium carbonate, or sodium bicarbonate can be combined into an aqueous solution of $Na_2PdCl_4.3H_2O$ and $NaAuCl_4.2H_2O$, and the resulting solution can be used to spray onto alumina pellets while they are being tumbled. Heating is used to dry the pelleted impregnated support and a subsequent washing step can be used to remove chloride ion, following by another drying step prior to calcining.

In one aspect, following the reduction step, it may be advantageous to contact or treat the alumina supported catalyst with an alkali metal acetate. For example, following the reduction step, the alumina supported catalyst can be contacted with a solution, such as an aqueous solution, of the acetate salt(s) comprising or selected from sodium acetate, potassium acetate, or various other acetate salts, or a combination thereof. Sample concentrations of the acetate salt or salts that can be used in aqueous solution are from about 0.02 wt % to about 15 wt %. Typically, the acetate salt or salts that can be used in aqueous solution from about 0.1 wt % to 10 wt % aqueous solution, such as, about 0.1 wt %, about 0.2 wt %, about 0.5 wt %, about 1 wt %, about 2 wt %, about 3 wt %, about 4 wt %, about 5 wt %, about 6 wt %, about 7 wt %, about 8 wt %, about 9 wt %, or about 10 wt %. Such parameters are well understood by the skilled artisan.

When prepared according to this disclosure, the resulting VAM catalyst can have a range of surface areas and bulk densities. For example, when prepared as described herein, the supported catalyst can have a surface area of from about 0.2 $m^2$/g to about 10 $m^2$/g. For example, the surface area can be from about from about 0.3 $m^2$/g to about 9 $m^2$/g, from about 0.4 $m^2$/g to about 8 $m^2$/g, from about 0.5 $m^2$/g to about 7 $m^2$/g, from about 1 $m^2$/g to about 6 $m^2$/g, or from about 1 $m^2$/g to about 5 $m^2$/g. The surface area of the catalysts prepared according to this disclosure can be greater than 10 $m^2$/g if desired, for example, surface areas from about 1 $m^2$/g to about 25 $m^2$/g are encompassed by this disclosure. When prepared as described herein, the supported catalyst also can have a packing density (sometimes referred to as apparent bulk density) of less than or about 1.35 g/mL. Alternatively, the supported catalyst also can have a bulk density of less than or about 1.3 g/mL, less than or about 1.25 g/mL, or less than or about 1.2 g/mL.

The supported palladium-gold catalyst preparation process uses the inert support as described herein that is impregnated with palladium and gold salts and, prior to the reduction, the impregnated support is calcined by heating in a non-reducing atmosphere. Using this process, it is possible to tailor the supported catalyst to encompass a wide range of selectivity and activity by varying conditions during the calcination and reduction. In one aspect to produce particularly high selectivity catalysts, the impregnated support is calcined in a non-reducing atmosphere at a temperature from about 350° C. to about 600° C. (alternatively, from about 450° C. to about 550° C.) prior to reduction which is typically carried out using hydrogen and at a temperature from about 350° C. to about 525° C. (alternatively, from about 450° C. to about 500° C.). In another aspect to produce particularly high activity catalysts, the impregnated support is calcined at a temperature from about 100° C. to about 350° C. (alternatively, from about 150° C. to about 275° C.) prior to reduction which can be carried out using hydrogen while gradually increasing the temperature up to a maximum of about 525° C.

While this disclosure has focused on tableted alumina, generally, any of the conventional inert support materials traditionally employed for palladium-gold catalysts for processes of this type are useful. For example, suitable supports include alumina, silica, silica-alumina, silica gel, silicic acid, silicates, titania, pumice, diatomaceous earth, silicon carbide and the like. In general, these inert supports or "catalyst carriers" can have pore volumes from 0.1 mL/g to 0.75 mL/g and surface areas from 0.5 $m^2$/g to 500 $m^2$/g; alternatively, pore volumes from 0.2 mL/g to 0.65 mL/g and surface areas from 1 $m^2$/g to 200 $m^2$/g.

Procedures to impregnate the inert support are generally known and understood by the skilled artisan. For example, typically the porous support material can be simultaneously or, more typically, successively treated with an aqueous solution of palladium and gold salts and an aqueous solution of an alkali metal compound which react on the support to form palladium and gold salts. The concentration of the solutions and the amount of each solution used can be governed by the concentration of palladium and gold desired in the final catalyst product. Water is then removed leaving the palladium and gold salts deposited on the support, and the dried support having the palladium and gold salts deposited thereon is then subjected to calcination and reduction in accordance with this disclosure.

In practice, a fixing agent may be contacted with the tablet while it is being impregnated, which is used to help bind the palladium compound and the gold compound to the tablet. Suitable fixing agents include alkali metal, alkaline earth metal, or ammonium compounds, for example, their hydroxides, carbonates, bicarbonates, metasilicates, and the like, and mixtures thereof. Any suitable impregnation method can be used to produce the impregnated tablet. The tablet may be simultaneously or successively impregnated with the palladium compound, the gold compound, and optionally a fixing agent. Preferably it is impregnated by contacting the support with an aqueous solution of these components, although other impregnating solvents may be used. The impregnated tablet is preferably washed with water or other solvents to remove any halide (e.g., chloride) from the tablet.

After impregnation of the support with the palladium compound, the gold compound, and the optional fixing agent, the impregnated support is then calcined, that is heated at an elevated temperature but below the melting point in a non-reducing atmosphere, before proceeding with the reduction. During calcination the palladium and gold salts impregnated on the support are decomposed or at least partially decomposed, the mode and extent of decomposition depending on the calcination conditions. Even though the calcination is carried out in a non-reducing atmosphere, some auto-reduction can occur, particularly for gold and particularly at lower temperatures. Additional procedures are found in U.S. Pat. Nos. 6,022,823 and 8,501,984, each of which is incorporated by reference in their entireties. U.S. Pat. No. 8,501,984 discloses a procedure for preparing a titania catalyst, which has been found to be particularly useful in the preparation of the alumina tableted catalysts of this disclosure.

Generally, the catalytic acetoxylation process can be performed in a gas phase, fixed bed tubular reactor using a catalyst prepared according to this disclosure, for example, at temperature from about 130° C. to about 250° C. and under a pressure from about 50 psia to about 150 psia. The amount of oxygen in the combined feed generally can be from about 5 mol % to about 15 mol %, and acetic acid can be introduced into the reactor in vapor form, being present from about 10 mol % to about 25 mol % in the combined feed. The amount of ethylene in the combined feed typically can be from about 65 mol % to about 80 mol %. Ethylene, oxygen and acetic acid are usually mixed and the mixture can then be fed into the reactor as a gas.

U.S. Patent Application Publication Nos. 2011/0087047 and 2011/0137075, which are incorporated herein by reference in their entireties, disclose processes for the separation and purification of the vinyl acetate monomer that can be used in the catalytic process with the catalysts of this disclosure. For example, these references disclose processes for producing vinyl acetate that includes contacting ethylene, acetic acid, and oxygen in the presence of a catalyst to produce a reaction mixture containing vinyl acetate, ethylene, carbon dioxide, acetic acid, water and ethylene glycol diacetate. The reaction mixture can be separated to a gas stream containing the ethylene, oxygen, and carbon dioxide and a crude vinyl acetate stream containing vinyl acetate, acetic acid, ethylene glycol diacetate, ethyl acetate and water. An ethylene glycol diacetate stream can be isolated from the crude vinyl acetate stream and hydrolyzed to recover the acetate content of the stream as acetic acid.

As an example, the reaction mixture using the disclosed catalysts can be withdrawn from the reactor and separated into a gas stream and a crude vinyl acetate stream. The gas stream can comprise ethylene and carbon dioxide. The crude vinyl acetate stream comprises vinyl acetate, acetic acid, water, ethyl acetate, and ethylene glycol diacetate. Carbon dioxide can be separated by distillation or absorption from ethylene, which is then preferably recycled to the acetoxylation reactor. The crude vinyl acetate stream can be separated by distillation into an ethylene glycol diacetate stream which includes ethylene glycol diacetate, acetic acid and water and a vinyl acetate product stream which comprises vinyl acetate and ethyl acetate. The vinyl acetate product stream can be subjected to further purification to produce vinyl acetate with a desired purity.

In addition to the embodiments and particular aspects of the catalysts and methods of this disclosure set out above, further embodiments according to this disclosure include the following.

Embodiment A. A process for preparing a supported palladium-gold catalyst, the process comprising:
a) impregnating an alumina support in tablet form having an average crush strength of greater than about 8 lbf/mm and less than about 12 lbf/mm and a pore volume (mercury intrusion porosimetry) from 0.25 mL/g to 0.35 mL/g with a palladium salt and a gold salt by contacting the support with an aqueous solution of [1] a palladium salt and a gold salt, and [2] an alkali metal hydroxide, alkali metal carbonate, alkali metal bicarbonate or alkali metal metasilicate to precipitate the palladium salt and the gold salt;
b) drying the impregnated support to remove water;
c) washing the impregnated support with water at a temperature at or above room temperature;
d) drying the impregnated support following washing;
e) calcining the dry impregnated support by heating it in an inert or oxidizing gas selected from helium, nitrogen, argon, neon, nitrogen oxides, oxygen, air and carbon dioxide at a temperature from 100° C. to 350° C. to decompose from 10 mol % to 70 mol % of the palladium salt and the gold salt, independently; and
f) reducing the calcined impregnated support in hydrogen or a mixture of hydrogen and an inert gas at a temperature from 100° C. to 550° C. to reduce the palladium and the gold to their respective metals.

Embodiment B. A process for preparing a supported palladium-gold catalyst, the process comprising:
a) impregnating an alumina support in tablet form having an average crush strength of greater than about 8 lbf/mm and less than about 12 lbf/mm and a pore volume (mercury intrusion porosimetry) from 0.25 mL/g to 0.35 mL/g with a palladium salt and a gold salt by contacting the support with an aqueous solution of [1] a palladium salt comprising $Na_2PdCl_4 \cdot 3H_2O$ and a gold salt comprising $NaAuCl_4 \cdot 2H_2O$, and [2] an alkali metal hydroxide, alkali metal carbonate, alkali metal bicarbonate or alkali metal metasilicate to precipitate the palladium salt and the gold salt;
b) drying the impregnated support to remove water;
c) washing the impregnated support with water at a temperature at or above room temperature;
d) drying the impregnated support following washing;
e) calcining the dry impregnated support by heating it in an inert or oxidizing gas selected from helium, nitrogen, argon, neon, nitrogen oxides, oxygen, air and carbon dioxide at a temperature greater than ambient to decompose at least a portion of the palladium salt and the gold salt, independently; and
f) reducing in hydrogen or a mixture of hydrogen and an inert gas at a temperature from 100° C. to 550° C. to convert the palladium and the gold to their respective metals.

Embodiment C. A process for the production of vinyl acetate, the process comprising contacting ethylene, acetic acid, and oxygen in the gas phase in the presence of a catalyst to produce a reaction mixture comprising vinyl acetate, the catalyst comprising:
a) an alumina support in tablet form having an average crush strength of greater than about 8 lbf/mm and less than about 12 lbf/mm and a pore volume (mercury intrusion porosimetry) from 0.28 mL/g to 0.35 mL/g;
b) from 0.2 wt % to 2.0 wt % palladium;

c) from 0.2 wt % to 1.5 wt % gold; and d) from 0.2 wt % to about 4 wt % of an alkali metal acetate.

Embodiment D. A process for preparing a supported catalyst as disclosed herein, wherein the supported catalyst displays a 0.5% increase in ethylene selectivity at 75% $O_2$ conversion for the vapor phase production of vinyl acetate by the reaction of ethylene, acetic acid and oxygen, as compared to the increase in ethylene selectivity at 75% $O_2$ conversion for a supported catalyst prepared under the same conditions using an alumina support in tablet form having an average crush strength of greater than 11 lbf/mm and a pore volume (HgPV) of 0.28 mL/g to 0.35 mL/g.

Embodiment E. A process for preparing a supported catalyst as disclosed herein, wherein the process provides a supported catalyst having any one or any combination of the following properties:

a) from 0.2 wt % to 2.0 wt % palladium metal;

b) from 0.2 wt % to 1.5 wt % gold metal;

c) a weight ratio of palladium to gold from 4:1 to 1:2;

d) a surface area of from about 0.2 $m^2$/g to about 10 $m^2$/g; and/or e) a packing density of less than about 1.35 g/mL.

Embodiment F. A process for preparing a supported catalyst as disclosed herein, wherein the tableted alumina support is further characterized by one or any combination of the following properties:

a) an average crush strength of greater than or about 9 lbf/mm and less than or about 11.5 lbf/mm;

b) a pore volume (HgPV) from 0.29 mL/g to 0.34 mL/g, or alternatively, from 0.30 mL/g to 0.35 mL/g;

c) a crystalline α-alumina content of greater than or about 95%;

d) a surface area of from 1 $m^2$/g to 25 $m^2$/g; and/or e) a pore size (diameter) distribution curve as measured by mercury intrusion porosimetry having relative maximums from about 0.05 to about 1 micrometers (μm).

EXAMPLES

The following general procedure, experimental details, and analytical methods, were used in developing the invention and characterizing the compositions prepared herein. Additional general procedures and examples of gas phase VAM processes can be found, for example, in U.S. Pat. Nos. 3,743,607, 4,119,567, 6,022,823, 8,399,700 and 8,501,984, each of which is incorporated herein by reference in their entireties.

Example 1

Catalyst Preparation

In a 100 mL beaker, $NaHCO_3$ powder (2.7 g (grams)) is slowly added to an aqueous solution containing $Na_2PdCl_4 \cdot 3H_2O$ (3.93 g), $NaAuCl_4 \cdot 2H_2O$ (1.05 g), and water (30 g). This mixture is stirred at room temperature for 10-15 min (minutes) to allow $CO_2$ to fully evolve. This solution is then sprayed with a small spray bottle onto alumina pellets (100 g) while they are being tumbled in a rotating flask. Once the impregnation is finished, the rotating flask is heated to about 100° C. with a heat gun. The impregnated pellets are tumbled for another 30 min at 100° C., then placed in an oven at 80° C. and dried overnight, after which they are cooled to room temperature.

The dried pellets are washed with warm deionized water (50-80° C.) until no chloride can be detected by precipitation with a 1 wt % silver nitrate solution. After washing is completed, the catalyst is dried at 80° C. to 100° C. to remove water. The catalyst pellets are then calcined at 230° C. for 3 hours in air. The calcined catalyst is subsequently reduced at 500° C. for 5 hours under a flow of 5 mol % hydrogen in an argon flow (10 mL/min/g), and subsequently cooled to room temperature. The reduced catalyst pellets are impregnated or promoted with an aqueous solution containing 8 wt % potassium acetate and 0.65 wt % potassium hydroxide. The promoted catalyst pellets are dried at 110° C. for 3 hours, to provide the palladium-gold catalyst. By elemental analysis, the catalyst contains 1.2 wt % Pd, 0.52 wt % Au, and 1.5 wt % K.

A commercial catalyst with the same metal loading is promoted as above and tested as a comparative example reference.

Example 2

Catalyst Testing

The palladium-gold catalyst prepared according to Example 1 is tested for vinyl acetate production in a fixed-bed reactor (stainless steel, 1 inch OD) according to the following procedure. The reactor is charged with a mixture of the catalyst (10 g) and inert glass beads (3 mm, 25 g). The reactor feed contains 50 mol % helium, 34 mol % ethylene, 12 mol % acetic acid, and 4 mol % oxygen. The reactor pressure is 80 psig and the space velocity relative to the volume of the catalyst is 2670 $h^{-1}$ at standard temperature and pressure. The reactor is heated and cooled using a circulated oil bath jacket, the temperature of which is set at 130° C.-150° C. The product stream is analyzed by online gas chromatography (GC). Oxygen conversion, oxygen selectivity, oxygen yield to vinyl acetate, oxygen reaction rate, and ethylene selectivity to vinyl acetate are calculated from the GC results. The vinyl acetate monomer catalyst test data obtained under these conditions using the palladium-gold catalysts prepared according to Example 1 is presented in Table 1.

TABLE 1

VAM catalyst test data

| Catalyst | Alumina Pellet Crush Strength, lbf/mm | Alumina Pellet Surface area, $m^2$/g | Alumina Pellet Total pore volume by Hg intrusion, mL/g | Reaction Rate ($Atm^{1/2}$)/sec at 150° C. |
|---|---|---|---|---|
| Q069 | 10.9 | 4.0 | 0.32 | 0.117 |
| Q070 | 17.3 | 3.1 | 0.29 | 0.100 |
| Q071 | 16.4 | 4.4 | 0.30 | 0.105 |
| Q072 | 13.0 | 4.2 | 0.31 | 0.104 |
| Q061 | 10.3 | 4.4 | — | 0.122 |

Further characterizations of the catalysts set out in Table 1 are provided in the figures. FIG. 1 illustrates the correlation between $O_2$ conversion (%) versus ethylene ($C_2H_4$) selectivity (%) for specific vinyl acetate monomer (VAM) catalysts, where it is seen that the catalysts designated Q069 and Q061 exhibited the best performance in ethylene selectivity as a function of oxygen conversion. As illustrated in Table 1, the best performance occurred when the alumina support tablets had a crush strength of about 10.5 lbf/mm.

Figure 4:
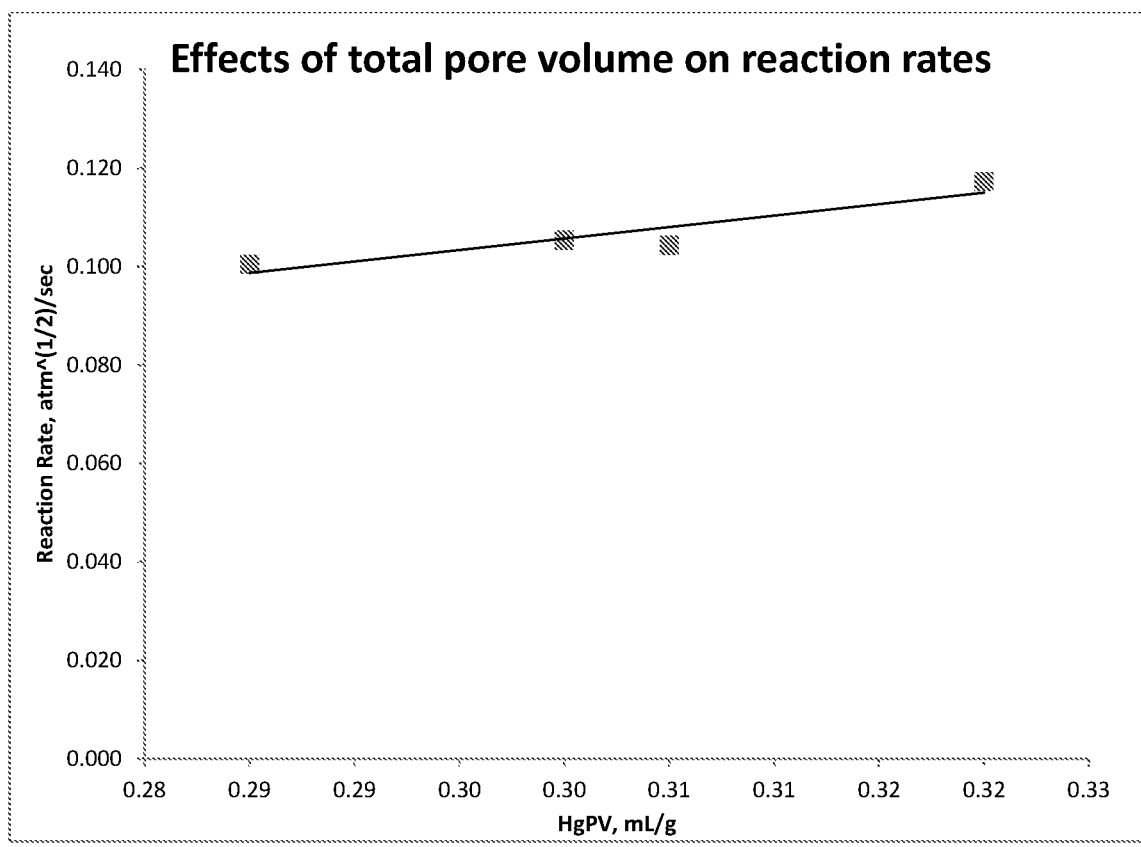
FIG. 4 illustrates the effect of total pore volume (HgPV, mL/g) on reaction rates ($atm^{1/2}$/sec at 150° C.) for the catalysts presented in Example 2 and Table 1.

The FIG. 2 data shows the effect of crush strength [lbf/mm (pound-force per millimeter), measured by ASTM 6175-03] on total pore volume (HgPV, mL/g) for the catalysts presented in Table 1. The drop off in total pore volume for the catalysts designated Q071 (16.4 lbf/mm) and Q070 (17.3 lbf/mm) that have the higher crush strengths is clear. Referring to FIG. 1, the performance of these catalyst is lower than the performance of catalysts having lower crush strengths. This unexpected discovery that catalyst performance diminishes when the crush strength of the catalyst is too high is significant. This aspect is dramatically shown in the FIG. 3 data, which illustrates the effect of crush strength (lbf/mm) on reaction rates ($atm^{1/2}$/sec at 150° C.) for the catalysts presented in Table 1. Thus, catalysts Q069 and Q061 have alumina pellet crush strengths of 10.9 lbf/mm and 10.3 lbf/mm, respectively, and these catalysts provide selectivity (FIG. 1) and reaction rates (FIG. 3) that are substantially improved over the catalysts prepared using alumina pellets having crush strengths of 13 lbf/mm and greater. Finally, FIG. 4 illustrates the effect of total pore volume (HgPV, mL/g) on reaction rates ($atm^{1/2}$/sec at 150° C.) for the catalysts presented in Table 1.

In summary, it has been discovered that catalyst performance showed a strong dependence on the crush strength of the catalyst, even to the extent that crush strengths that are too high are detrimental to catalyst performance and selectivity. Crush strength is closely related to the porosity of the catalyst carrier or support, and that porosity can be controlled with respect to the forming and sintering conditions.

To define more clearly the terms used herein, the following definitions are provided, and unless otherwise indicated or the context requires otherwise, these definitions are applicable throughout this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied.

The disclosures of various publications that may be referenced throughout this specification, which are hereby incorporated by reference in pertinent part in order to more fully describe the state of the art to which the disclosed subject matter pertains. To the extent that any definition or usage provided by any document incorporated herein by reference conflicts with the definition or usage provided herein, the definition or usage provided herein controls.

For any particular compound disclosed herein, the general structure presented is also intended to encompasses all conformational isomers and stereoisomers that can arise from a particular set of substituents, unless indicated otherwise or the context provides otherwise. Thus, the general structure encompasses all enantiomers, diastereomers, and other optical isomers whether in enantiomeric or racemic forms, as well as mixtures of stereoisomers, as the context permits or requires. Accordingly, Applicant reserves the right to proviso out any particular individual isomer or isomers, if for any reason Applicant chooses to claim less than the full measure of the disclosure, for example, to account for a reference that Applicant is unaware of at the time of the filing of the application.

Throughout the specification and claims, the word "comprise" and variations of the word, such as "comprising" and "comprises," means "including but not limited to," and is not intended to exclude, for example, other additives, components, elements, or steps. While methods and features are described in terms of "comprising" various steps or components, these methods and features can also "consist essentially of" or "consist of" the various steps or components. Therefore, by the disclosure that a composition, a method, and the like "comprises" one or more elements or steps, Applicant also intends to disclose that the composition, the method, and the like may also "consist essentially of" or "consist of" the recited elements or steps.

As used in the specification and the claims, the singular forms "a," "an," and "the" include plural referents unless the context clearly indicates otherwise. Thus, for example, reference to "a compound" includes mixtures of two or more such compounds, reference to "the composition" includes mixtures of two or more such compositions, and the like.

"Optional" or "optionally" means that the subsequently described event or circumstance can or cannot occur, and that the description includes instances where the event or circumstance occurs and instances where it does not.

The terms "tablet" and "pellet" are used interchangeably, as understood by the person of ordinary skill in the art, as are related words such as "tableted" and "pelletized".

Unless indicated otherwise, when a range of any type is disclosed or claimed, for example a range of the percentages, crush strengths, conversions or reaction rates, and the like, it is intended to disclose or claim individually each possible number that such a range could reasonably encompass, including any sub-ranges or combinations of sub-ranges encompassed therein. For example, when describing a range of percentages such as from 85% to 95%, it is understood that this disclosure is intended to encompass each of 85%, 86%, 87%, 88%, 89%, 90%, 91%, 92%, 93%, 94%, and 95%, as well as any ranges, sub-ranges, and combinations of sub-ranges encompassed therein. Applicant's intent is that these two methods of describing the range are interchangeable. Accordingly, Applicant reserves the right to proviso out or exclude any individual members of any such group, including any sub-ranges or combinations of sub-ranges within the group, if for any reason Applicant chooses to claim less than the full measure of the disclosure, for example, to account for a reference that Applicant is unaware of at the time of the filing of the application.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed herein, and that each value is also herein disclosed as "about" that particular value in addition to the value itself. In aspects, "about" can be used to mean within 10% of the recited value, within 5% of the recited value, within 2% of the recited value, or within 1% of the recited value.

Any headings that are employed herein are not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

Applicants reserve the right to proviso out any selection, feature, range, element, or aspect, for example, to limit the scope of any claim to account for a prior disclosure of which Applicants may be unaware.

These and other features, advantages and embodiments of the invention disclosed herein will be readily apparent to those exercising ordinary skill after reading the foregoing disclosures. Accordingly, while specific embodiments of the invention have been described in considerable detail, variations and modifications of those embodiments can be effected without departing from the spirit and scope of the invention as claimed.

We claim:

1. A process for preparing a supported catalyst, the process comprising:
   a) providing an alumina support in tablet form having an average crush strength of greater than about 8 lbf/mm and less than about 12 lbf/mm, a pore volume (mercury intrusion porosimetry, HgPV) from 0.25 mL/g to 0.35 mL/g, and a crystalline α-alumina content of greater than 93%;
   b) contacting the alumina support with a composition to provide an impregnated alumina support, the composition comprising [1] a palladium salt and a gold salt, and [2] a fixing agent selected from an alkali metal, an alkaline earth metal, or an ammonium compound of hydroxide, carbonate, bicarbonate, or metasilicate, or any combination thereof;
   c) calcining the impregnated alumina support in a non-reducing atmosphere for a time and a temperature sufficient to at least partially decompose the palladium salt and the gold salt; and
   d) reducing the calcined impregnated alumina support comprising partially decomposed palladium and gold salts with a reducing agent for a time and a temperature sufficient to provide a supported catalyst comprising palladium metal and gold metal.

2. A process for preparing a supported catalyst according to claim 1, further comprising after the contacting step, the steps of [b1] drying the impregnated alumina support; [b2] washing the impregnated alumina support with water; and [b3] drying the impregnated alumina support following washing.

3. A process for preparing a supported catalyst according to claim 1, wherein the fixing agent is selected from the sodium salt or the potassium salt of carbonate ion or bicarbonate ion, or any combination thereof.

4. A process for preparing a supported catalyst according to claim 1, wherein the calcining step temperature is from about 100° C. to about 600° C. and/or wherein from about 10 mol % to about 70 mol % of the palladium salt and the gold salt, independently, are decomposed.

5. A process for preparing a supported catalyst according to claim 1, wherein following the reducing step, the supported catalyst is contacted with an alkali metal acetate.

6. A process for preparing a supported catalyst according to claim 1, wherein following the reducing step, the supported catalyst is contacted with 0.1 wt % to 10 wt % aqueous solution of the acetate salt(s) comprising sodium acetate, potassium acetate, or a combination thereof.

7. A process for preparing a supported catalyst according to claim 1, wherein the process provides a supported catalyst having any one or any combination of the following properties:
   a) from 0.2 wt % to 2.0 wt % palladium metal;
   b) from 0.2 wt % to 1.5 wt % gold metal;
   c) a weight ratio of palladium to gold from 4:1 to 1:2;
   d) a surface area of from about 0.2 $m^2$/g to about 10 $m^2$/g; and/or
   e) a packing density of less than about 1.35 g/mL.

8. A process for preparing a supported catalyst according to claim 1, wherein the palladium salt is selected from palladium chloride, sodium chloropalladite, palladium nitrate and palladium sulfate, and the gold salt is selected from auric chloride, tetrachloroauric acid and sodium tetrachloroaurate.

9. A process for preparing a supported catalyst according to claim 1, wherein the alumina support in tablet form is further characterized by one or any combination of the following properties:
   a) an average crush strength of greater than or about 9 lbf/mm and less than or about 11.5 lbf/mm;
   b) a pore volume (HgPV) from 0.28 mL/g to 0.35 mL/g;
   c) a crystalline α-alumina content of greater than or about 95%;
   d) a surface area of from 1 $m^2$/g to 25 $m^2$/g; and/or
   e) a pore size (diameter) distribution curve as measured by mercury intrusion porosimetry having relative maximums from about 0.05 to about 1 micrometer (μm).

10. A process for preparing a supported catalyst according to claim 9, wherein the alumina support in tablet form has an average crush strength of from about 10 lbf/mm to about 11 lbf/mm and/or a pore volume (HgPV) from 0.29 mL/g to 0.34 mL/g.

11. A process for preparing a supported catalyst according to claim 1, wherein the non-reducing atmosphere is an inert or oxidizing gas selected from helium, nitrogen, argon, neon, nitrogen oxides, oxygen, air and carbon dioxide.

12. A process for preparing a supported catalyst according to claim 1, wherein the reducing step temperature is from ambient to about 550° C. and the reducing agent comprises hydrogen, carbon monoxide, hydrocarbons, aldehydes, alcohols, ammonia, hydrazine, primary amines, carboxylic acids, carboxylic acid salts or carboxylic acid esters.

13. A process for preparing a supported catalyst according to claim 1, wherein the impregnated support is calcined at a temperature from 350° C. to 600° C. and/or wherein at least 70 mol % of the palladium salt and at least 70 mol % of the gold salt are decomposed.

14. A process for preparing a supported catalyst according claim 1, wherein the supported catalyst displays a 0.5% increase in ethylene selectivity at 75% $O_2$ conversion for the vapor phase production of vinyl acetate by the reaction of ethylene, acetic acid and oxygen, as compared to the increase in ethylene selectivity at 75% $O_2$ conversion for a supported catalyst prepared under the same conditions using an alumina support in tablet form having an average crush strength of greater than 11 lbf/mm and a pore volume (HgPV) of 0.28 mL/g to 0.35 mL/g.

15. A process for preparing a supported palladium-gold catalyst, the process comprising:
   a) impregnating an alumina support in tablet form having an average crush strength of greater than about 8 lbf/mm and less than about 12 lbf/mm and a pore volume (mercury intrusion porosimetry) from 0.25 mL/g to 0.35 mL/g, and a crystalline α-alumina content of greater than 93%, with a palladium salt and a gold salt by contacting the support with an aqueous solution of [1] a palladium salt and a gold salt, and [2] an alkali metal hydroxide, alkali metal carbonate, alkali metal bicarbonate or alkali metal metasilicate to precipitate the palladium salt and the gold salt;
   b) drying the impregnated support to remove water;
   c) washing the impregnated support with water at a temperature at or above room temperature;
   d) drying the impregnated support following washing;
   e) calcining the dry impregnated support by heating it in an inert or oxidizing gas selected from helium, nitrogen, argon, neon, nitrogen oxides, oxygen, air and carbon dioxide at a temperature from 100° C. to 350°

C. to decompose from 10 mol % to 70 mol % of the palladium salt and the gold salt, independently; and f) reducing the calcined impregnated support in hydrogen or a mixture of hydrogen and an inert gas at a temperature from 100° C. to 550° C. to reduce the palladium and the gold to their respective metals.

16. A process for preparing a supported catalyst according to claim 15, wherein the palladium salt is selected from palladium chloride, sodium chloropalladite, palladium nitrate and palladium sulfate, and the gold salt is selected from auric chloride, tetrachloroauric acid and sodium tetrachloroaurate.

17. A process for preparing a supported catalyst according to claim 15, wherein the alumina support in tablet form is further characterized by one or any combination of the following properties:

a) an average crush strength of greater than or about 9 lbf/mm and less than or about 11.5 lbf/mm;

b) a pore volume (HgPV) from 0.28 mL/g to 0.35 mL/g;

c) a crystalline α-alumina content of greater than or about 95%;

d) a surface area of from 1 m²/g to 25 m²/g; and/or e) a pore size (diameter) distribution curve as measured by mercury intrusion porosimetry having relative maximums from about 0.05 to about 1 micrometers (μm).

18. A process for preparing a supported catalyst according to claim 15, wherein the alumina support in tablet form has an average crush strength of from about 10 lbf/mm to about 11 lbf/mm and/or a pore volume (HgPV) from 0.29 mL/g to 0.34 mL/g.

19. A process for preparing a supported catalyst according to claim 15, wherein the process provides a supported catalyst having any one or any combination of the following properties:

a) the supported catalyst comprises from 0.1 wt % to 3.0 wt % palladium;

b) the supported catalyst comprises from 0.1 wt % to 3.0 wt % gold; and/or c) the supported catalyst has a weight ratio of palladium to gold from 5:1 to 1:3.

20. A process for preparing a supported catalyst according to claim 15, wherein the process provides a supported catalyst comprises from 0.2 wt % to 2.0 wt % palladium, from 0.2 wt % to 1.5 wt % gold, and has a weight ratio of palladium to gold from 4:1 to 1:2.

* * * * *